(12) United States Patent
Lampropoulos et al.

(10) Patent No.: US 9,539,016 B2
(45) Date of Patent: Jan. 10, 2017

(54) MULTIPLE LOOP SNARE

(71) Applicant: Merit Medical Systems, Inc., South Jordan, UT (US)

(72) Inventors: Fred Lampropoulos, Salt Lake City, UT (US); Jim Mottola, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 93 days.

(21) Appl. No.: 14/202,235

(22) Filed: Mar. 10, 2014

(65) Prior Publication Data

US 2014/0188124 A1 Jul. 3, 2014

Related U.S. Application Data

(62) Division of application No. 13/343,570, filed on Jan. 4, 2012, now Pat. No. 8,974,470.

(60) Provisional application No. 61/429,691, filed on Jan. 4, 2011.

(51) Int. Cl.
*A61B 17/24* (2006.01)
*A61B 17/221* (2006.01)
*A61B 17/3205* (2006.01)
*A61B 17/50* (2006.01)
*A61B 17/00* (2006.01)
*A61B 17/22* (2006.01)

(52) U.S. Cl.
CPC ....... *A61B 17/221* (2013.01); *A61B 17/32056* (2013.01); *A61B 17/50* (2013.01); *A61B 2017/00358* (2013.01); *A61B 2017/22035* (2013.01); *F04C 2270/0421* (2013.01)

(58) Field of Classification Search
CPC ............... A61B 17/221; A61B 2017/2212; A61B 2017/2217; A61B 17/225; A61B 17/22031; A61B 17/50; A61B 17/32056
USPC ............ 606/2.5, 113, 114, 127, 128
See application file for complete search history.

(56) References Cited

U.S. PATENT DOCUMENTS

| 4,612,931 A | 9/1986 | Dormia |
|---|---|---|
| 5,171,233 A | 12/1992 | Amplatz et al. |
| 5,290,294 A | 3/1994 | Cox et al. |
| 5,352,219 A | 10/1994 | Reddy |
| 5,417,684 A | 5/1995 | Jackson et al. |
| 5,460,610 A | 10/1995 | Don Michael |
| 5,486,183 A * | 1/1996 | Middleman ............ A61B 10/02 606/113 |

(Continued)

FOREIGN PATENT DOCUMENTS

| EP | 0169784 | 7/1985 |
|---|---|---|
| EP | 1757234 | 7/2006 |

(Continued)

OTHER PUBLICATIONS

Office Action dated Jun. 10, 2014 for U.S. Appl. No. 13/343,570.

(Continued)

*Primary Examiner* — Tuan V Nguyen
(74) *Attorney, Agent, or Firm* — Stoel Rives LLP (57) ABSTRACT

A snare device comprising multiple loops is described. The loops may be configured having various sizes or shapes and may be configured for use within a single outer sheath. Each loop provided in connection with a single snare device may have a different size, shape, disposition, or orientation than other loops associated with the same snare device.

17 Claims, 10 Drawing Sheets

(56) References Cited

U.S. PATENT DOCUMENTS

| | | | |
|---|---|---|---|
| 5,562,678 | A | 10/1996 | Booker |
| 5,613,973 | A | 3/1997 | Jackson et al. |
| 5,782,839 | A | 7/1998 | Hart et al. |
| 5,860,987 | A | 1/1999 | Ratcliff et al. |
| 5,911,725 | A | 6/1999 | Boury |
| 5,961,526 | A | 10/1999 | Chu et al. |
| 5,971,994 | A | 10/1999 | Fritzsch |
| 6,059,796 | A | 5/2000 | Bilitz et al. |
| 6,071,233 | A | 6/2000 | Ishikawa et al. |
| 6,093,195 | A | 7/2000 | Ouchi |
| 6,174,318 | B1 | 1/2001 | Bates et al. |
| 6,193,672 | B1 | 2/2001 | Clement |
| 6,458,145 | B1 | 10/2002 | Ravenscroft et al. |
| 6,517,550 | B1 | 2/2003 | Konya et al. |
| 8,974,470 | B2 * | 3/2015 | Lampropoulos ..... A61B 17/221 606/113 |
| 2002/0123698 | A1 | 9/2002 | Garibotto et al. |
| 2002/0123765 | A1 | 9/2002 | Sepetka et al. |
| 2002/0183781 | A1 | 12/2002 | Casey et al. |
| 2002/0188262 | A1 | 12/2002 | Abe |
| 2003/0021446 | A1 | 1/2003 | Dietz et al. |
| 2004/0059345 | A1 | 3/2004 | Nakao et al. |
| 2004/0068226 | A1 | 4/2004 | Brannon |
| 2004/0122445 | A1 * | 6/2004 | Butler ............ A61B 17/22031 606/127 |
| 2004/0153095 | A1 | 8/2004 | Seddon |
| 2004/0153096 | A1 | 8/2004 | Goode et al. |
| 2005/0171566 | A1 | 8/2005 | Kanamaru |
| 2005/0209609 | A1 | 9/2005 | Wallace |
| 2005/0234474 | A1 | 10/2005 | DeMello et al. |
| 2006/0009800 | A1 | 1/2006 | Christianson et al. |
| 2006/0090761 | A1 | 5/2006 | Kurrus |
| 2006/0116702 | A1 * | 6/2006 | Goto .................. A61B 17/221 606/159 |
| 2007/0129719 | A1 | 6/2007 | Kendale et al. |
| 2007/0162047 | A1 | 7/2007 | Gasche |
| 2007/0162048 | A1 | 7/2007 | Quinn et al. |
| 2007/0191866 | A1 | 8/2007 | Palmer et al. |
| 2007/0260264 | A1 | 11/2007 | Nobis et al. |
| 2008/0086149 | A1 | 4/2008 | Diamant et al. |
| 2008/0188866 | A1 | 8/2008 | Karpiel et al. |
| 2009/0030427 | A1 | 1/2009 | Razvi et al. |
| 2009/0069806 | A1 | 3/2009 | De La Mora Levy et al. |
| 2009/0112244 | A1 | 4/2009 | Freudenthal |
| 2009/0118760 | A1 | 5/2009 | Clausen et al. |
| 2009/0131749 | A1 | 5/2009 | Ahmed et al. |
| 2010/0087781 | A1 | 4/2010 | Adams et al. |
| 2012/0029526 | A1 | 2/2012 | Hewitt et al. |
| 2012/0289945 | A1 | 11/2012 | Segermark et al. |
| 2012/0289971 | A1 | 11/2012 | Segermark et al. |
| 2013/0006261 | A1 | 1/2013 | Lampropoulos et al. |
| 2013/0006262 | A1 | 1/2013 | Lampropoulos et al. |

FOREIGN PATENT DOCUMENTS

| | | |
|---|---|---|
| JP | 2002209909 | 7/2002 |
| JP | 2005198931 | 7/2005 |
| JP | 2005270464 | 10/2005 |
| WO | WO94/20029 | 9/1994 |
| WO | WO02/43600 | 6/2002 |
| WO | WO2008/045143 | 4/2008 |
| WO | 2009021104 A2 | 2/2009 |
| WO | WO2009/021104 | 2/2009 |
| WO | WO2010/002549 | 1/2010 |

OTHER PUBLICATIONS

Extended European Search Report dated Aug. 6, 2014 for EP12732501.7.
International Search Report and Written Opinion dated Mar. 18, 2011 for PCT/US2011/022509.
International Search Report and Written Opinion dated May 1, 2012 for PCT/US2012/020204.
International Search Report and Written Opinion dated May 3, 2012 for PCT/US2012/020208.
International Search Report and Written Opinion dated Aug. 13, 2012 for PCT/US2012/36144.
International Search Report and Written Opinion dated Aug. 16, 2012 for PCT/US2012/36125.
Office Action dated Aug. 17, 2012 for U.S. Appl. No. 13/014,427.
Office Action dated Mar. 13, 2013 for U.S. Appl. No. 13/105,653.
Office Action dated Mar. 28, 2013 for U.S. Appl. No. 13/343,570.
Office Action dated Apr. 15, 2013 for U.S. Appl. No. 13/014,427.
Office Action dated Jul. 19, 2013 for U.S. Appl. No. 13/343,570.
Notice of Allowance dated Oct. 9, 2013 for U.S. Appl. No. 13/014,427.
Extended European Search Report dated Mar. 31, 2014 for EP 12732457.2.
Office Action dated Apr. 29, 2014 for U.S. Appl. No. 13/343,550.
Notice of Allowance dated Dec. 12, 2014 for U.S. Appl. No. 13/343,570.
Notice of Allowance dated Mar. 16, 2015 for U.S. Appl. No. 13/106,995.
European Search Report dated Mar. 30, 2015 for EP 11737545.1.
Extended European Search Report dated Jun. 9, 2015 for EP12786215.9.
Extended European Search Report dated Aug. 6, 2014 EP12732501.7.
Extended European Search Report Received dated Mar. 30, 2015 EP11737545.1.
Office Action dated Mar. 13, 2014 for U.S. Appl. No. 13/106,995.
Office Action dated Sep. 26, 2012 for U.S. Appl. No. 13/106,995.

* cited by examiner

MULTIPLE LOOP SNARE

RELATED APPLICATIONS

This application is a divisional of U.S. patent application Ser. No. 13/343,570, now issued as U.S. Pat. No. 8,974,470, entitled "Multiple Loop Snare," filed on Jan. 4, 2012, which claims the benefit of U.S. Provisional Application No. 61/429,691, filed on Jan. 4, 2011, the contents of each of which are fully incorporated herein by reference.

TECHNICAL FIELD

The present disclosure relates generally to medical devices configured for use within the human body. Specifically, the present disclosure relates to snare devices which may comprise multiple loops.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Snares may be utilized as part of certain therapies, including minimally invasive therapies. For instance, a snare may be used to capture a foreign object located within a body lumen, such as within the vasculature. Snares of various sizes may be utilized depending on, for example, the type or nature of the therapy, the location of the therapy within the body, and so on. As further described below, the present disclosure relates to snare devices which may include multiple loops including embodiments with loops having different sizes.

In some instances a multiple snare loop snare device may simply certain medical procedures or therapies by allowing a practitioner to deploy snare loops of different sizes, shapes, orientations, for example, without completely removing the snare device and inserting an alternate snare device.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

As used herein a "snare device" generally refers to an elongate instrument comprising a snare loop. Snare devices, as described herein, may further include additional components, such as an outer sheath, for example, though these components are not required. Additionally, a "snare loop" need not be arcuate or circular in shape, but may be any shape enclosed by a loop of material, for example by a wire.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner during use, while the distal end is the opposite end. For example, the proximal end of a snare device refers to the end nearest the practitioner when the snare device is in use.

Figure 1A:
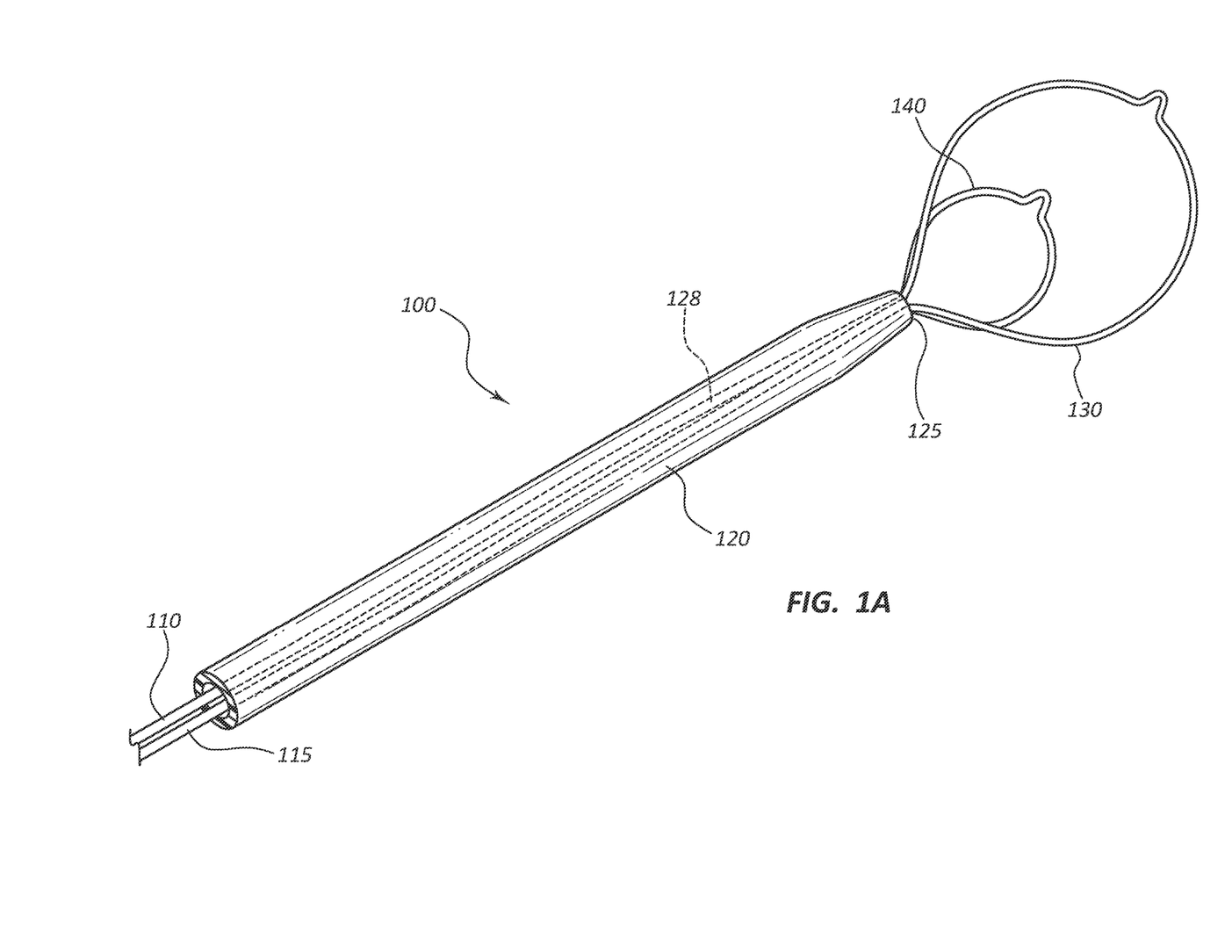
FIG. 1A is a perspective view of a snare device comprising two snare loops.

FIG. 1A is a perspective view of a snare device 100 comprising two snare loops 130, 140. In the illustrated embodiment, the first snare loop 130 is coupled to a first elongate shaft 110 and the second snare loop 140 is coupled to a second elongate shaft 115. The illustrated snare device 100 further comprises an outer sheath 120 which comprises a sheath lumen 128 and a distal opening 125 in communication with the sheath lumen 128. The elongate shafts 110, 115 may be longitudinally displaceable with respect to the outer sheath 120, allowing the first snare loop 130 and the second snare loop 140 to be deployable and retractable through the distal opening 125 in the outer sheath 120. Thus, depending on the position of either elongate shaft 110, 115 with respect to the outer sheath 120, each of the first snare loop 130 and the second snare loop 140 may be completely within the outer sheath 120 (or fully retracted), completely outside of the outer sheath 120 (or fully deployed), or partially within the outer sheath 120 (or partially deployed/retracted). In some embodiments, each of the two elongate shafts 110, 115 move independently of each other.

It will be appreciated by those of skill in the art having the benefit of this disclosure, that the illustrated embodiment may be combined with numerous handles or other devices capable of displacing the elongate shafts 110, 115 with respect to the outer sheath 120. In particular, the outer sheath 120 and each elongate shaft 110, 115 may each be coupled to different parts of a handle component. The handle component may include a body coupled to the outer sheath 120 and sliding members coupled to the elongate shafts 110, 115. As the sliding members are displaced relative to the handle body, the elongate shafts 110, 115 may be displaced relative to the outer sheath 120. This may be accomplished by any method known in the art, including methods and devices which would enable the user to manipulate one or both elongate shafts 110, 115 with one hand. The handle may also be equipped with a single sliding member and a toggle switch or rotating knob to move the first 130 and second 140 snare loops in an articulating manner (back and forth opposed to each other). When the toggle switch is a first position the sliding member may be configured to manipulate the position of the first elongate shaft 110 and when the toggle switch is in a second position the sliding member may be configured to manipulate the position of the second elongate shaft 115. Any handle or handle like member known in the art may be used, including handles with sliding members, rotating members, or any other member configured to displace the elongate shafts 110, 115.

Figure 1B:
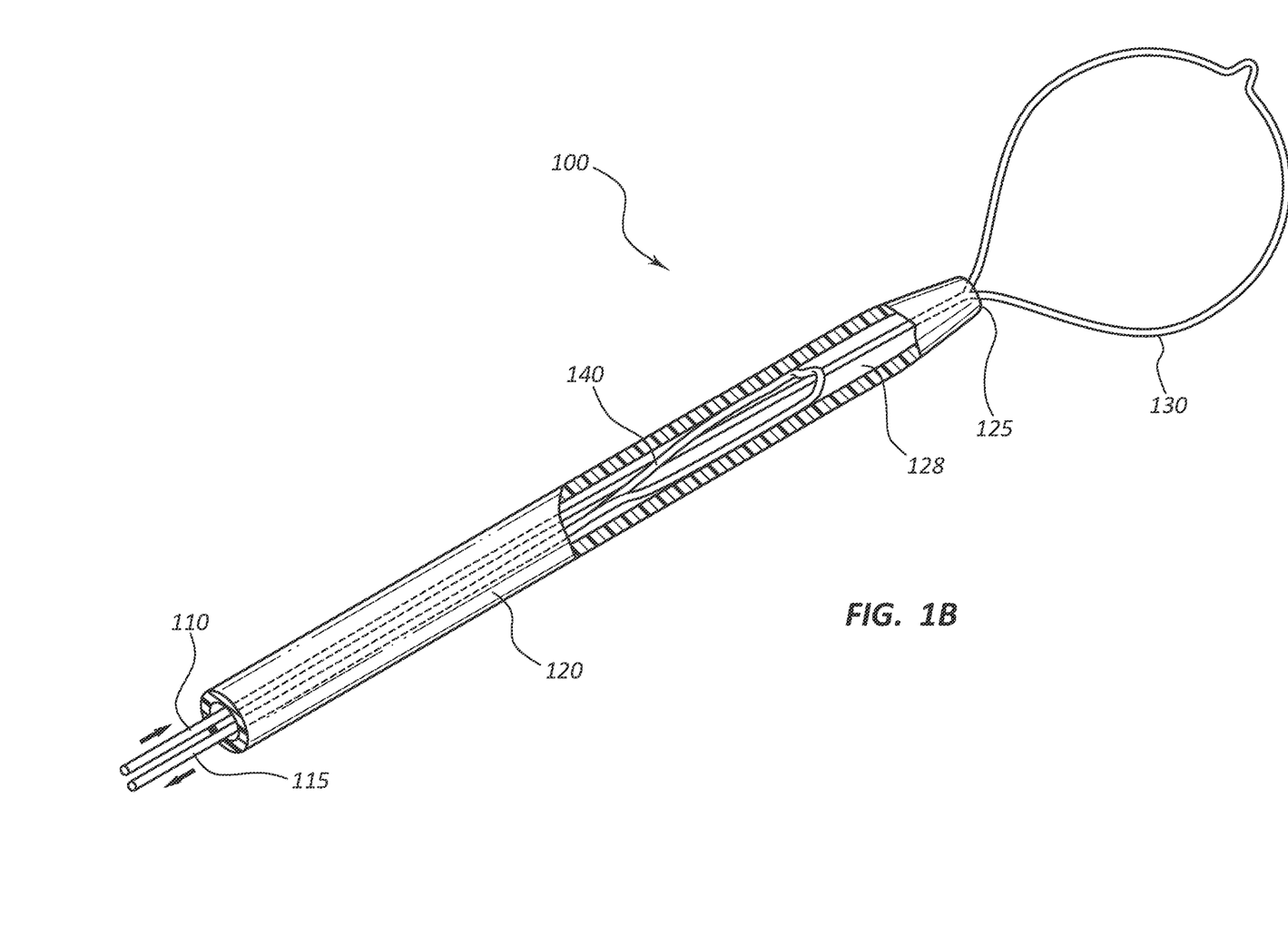
FIG. 1B is a perspective view of the snare device of FIG. 1A in a second configuration.

In the configuration illustrated in FIG. 1A, both the first snare loop 130 and the second snare loop 140 are shown deployed from the outer sheath 120. FIG. 1B is a perspective view of the snare device 100 of FIG. 1A in a second configuration, wherein the first snare loop 130 is fully deployed from the outer sheath 120 and the second snare loop 140 is fully retracted within the sheath lumen 128. The arrows indicate how displacement of the first elongate shaft 110 and the second elongate shaft 115 with respect to the outer sheath 120 may deploy and/or retract the first 130 and second 140 snare loops, respectively.

Figure 1C:
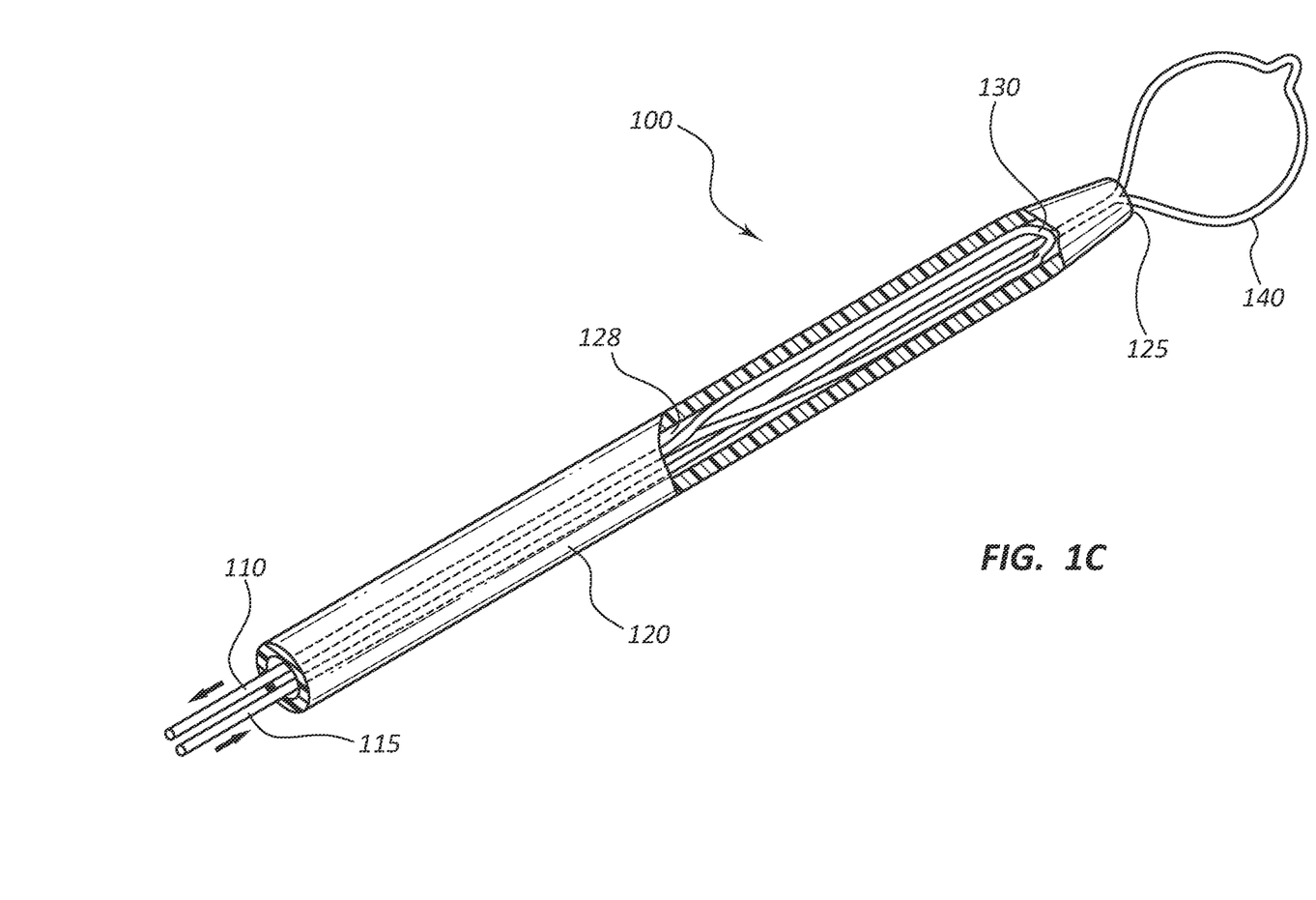
FIG. 1C is a perspective view of the snare device of FIGS. 1A and 1B in a third configuration.

FIG. 1C is a perspective view of the snare device 100 of FIGS. 1A and 1B in a third configuration, wherein the second snare loop 140 is fully deployed and the first snare loop 130 is fully retracted within the sheath lumen 128 of the outer sheath 120. Again, the arrows indicate how displacement of the first elongate shaft 110 and the second elongate shaft 115 with respect to the outer sheath 120 may deploy and/or retract the first 130 and second 140 snare loops, respectively.

In some embodiments, the elongate shafts 110, 115 and snare loops 130, 140 may be formed of a variety of materials known in the art, including Nitinol. Nitinol and other "shape memory" materials may be used in applications where a particular shaped snare loop is desired. In certain embodiments, one or both of the first 130 and second 140 snare loops may be disposed in one or more planes which are substantially perpendicular to the axial direction of the elongate shafts 110, 115 when the snare loops 130, 140 are fully deployed or otherwise unconstrained.

A snare device, such as device 100 of FIGS. 1A-1C may be configured for use in applications where the precise size or shape of the necessary snare cannot be determined prior to beginning the procedure or other instances wherein flexibility regarding characteristics of the snare loops (such as size or shape) may be desirable. During use, a practitioner may first attempt to perform the desired therapy with one of the two loops, then retract that loop and attempt to perform the therapy with the second of the two loops. Loops of differing sizes and shapes may allow a practitioner flexibility during the procedure to use alternatively sized or shaped snare loops without removing the entire snare and inserting a second separate snare.

In the illustrated embodiment, the first snare loop 130 is relatively larger than the second snare loop 140. In other embodiments, the two loops, additionally or alternatively, may be configured with different shapes, formed of different materials, and so on. Furthermore, it will be appreciated by one of skill in the art with the benefit of this disclosure, that the snare device 100 of FIGS. 1A-1C may alternatively be configured with more than two elongate shafts and/or more than two snare loops; including embodiments where multiple loops are coupled to one elongate shaft.

Figure 2A:
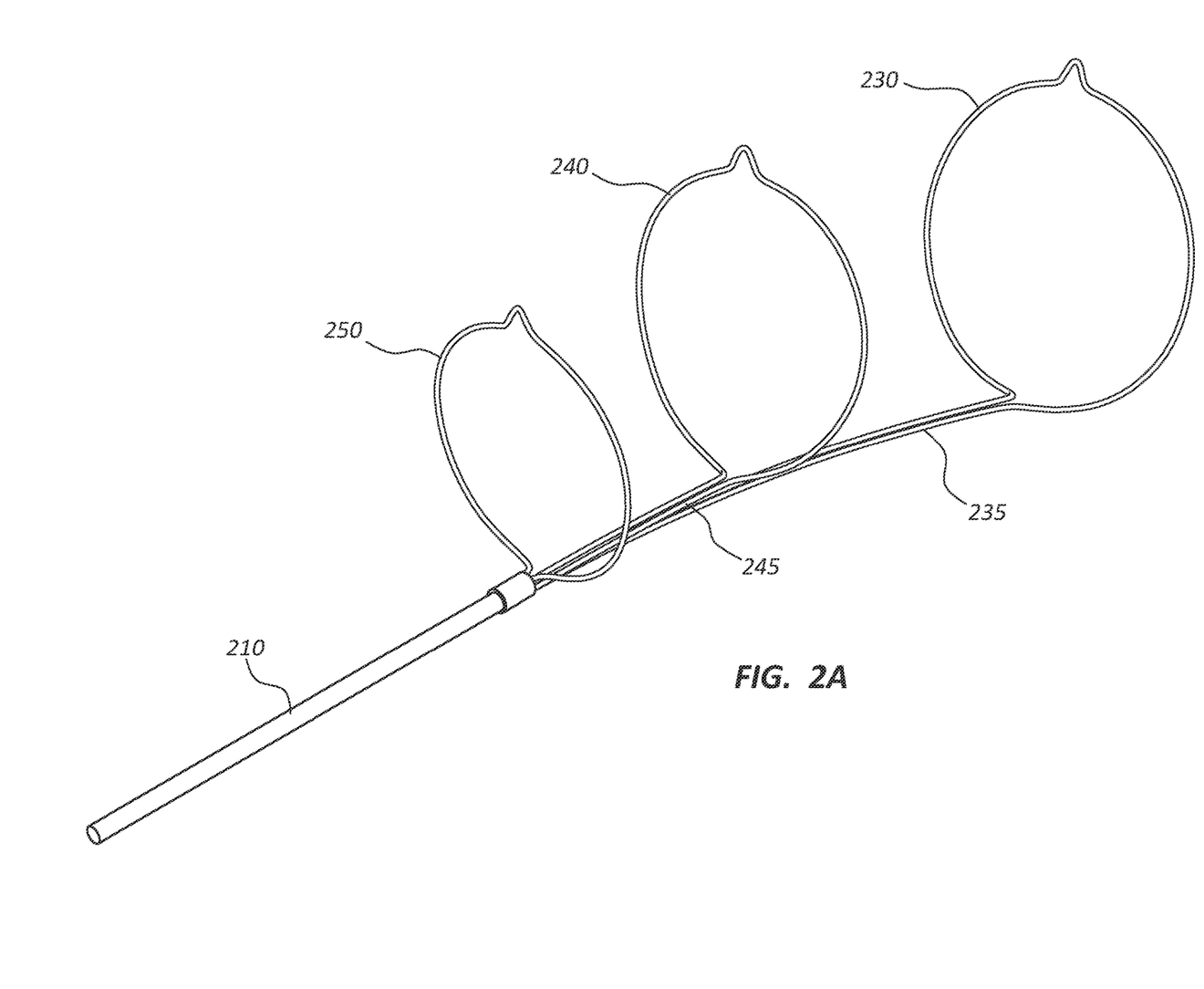
FIG. 2A is a perspective view of a snare device comprising three snare loops each coupled to an elongate shaft.

FIG. 2A is a perspective view of another embodiment of a snare device that can, in certain respects, resemble components of the snare device described in connection with FIGS. 1A-1C above. It will be appreciated that all the illustrated embodiments may have analogous features. Accordingly, like features are designated with like reference numerals, with the leading digits incremented to "2." (For instance, the elongate shaft is designated "110" in FIG. 1A, and an analogous elongate shaft is designated as "210" in FIG. 2A.) Relevant disclosure set forth above regarding similarly identified features thus may not be repeated hereafter. Moreover, specific features of the snare device and related components shown in FIG. 2A may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the snare device of FIG. 2A. Any suitable combination of the features, and variations of the same, described with respect to the snare device and components illustrated in FIGS. 1A-1C, can be employed with the snare device and components of FIG. 2A, and vice versa. This pattern of disclosure applies equally to further embodiments depicted in subsequent figures and described hereafter.

Moreover, disclosure related herein in connection to any particular embodiment may be analogously applicable to other embodiments. For example, disclosure related to general snare operation, including displacement of a snare loop or elongate shaft with respect to an outer sheath, deployment or retraction of a snare loop, and/or use of a snare loop in therapy may be analogously applicable to all embodiments, notwithstanding the disclosure being included in connection with any particular embodiment.

FIG. 2A is a perspective view of a snare device comprising three snare loops 230, 240, 250 each coupled to an elongate shaft 210. More specifically, in the illustrated embodiment, a first snare loop 230, a second snare loop 240, and a third snare loop 250 are each coupled to the elongate shaft 210. In the illustrated embodiment, the first snare loop 230 is relatively larger than the second 240 and third 250 snare loops. Further, the loops are disposed in descending order of size from the distal most position to the proximal most position. In other embodiments, this order may be modified, for example, the smallest loop may be in the distal most position and/or the loops may not be arranged in sequential order by size.

In the embodiment of FIG. 2A, the first snare loop 230 is coupled to the elongate shaft 210 by a first intermediate portion 235 and the second snare loop 240 is coupled to the elongate shaft 210 by a second intermediate portion 245. In the illustrated embodiment the intermediate portions 235, 245 are substantially coaxially aligned with the longitudinal axis of the elongate shaft 210. Additionally, each of the snare loops 230, 240, 250 are disposed substantially perpendicular to the longitudinal axis of the elongate shaft 210 when the snare loops 230, 240, 250 are in an unconstrained state. The lengths of the intermediate portions 235, 245 may control the offset of each loop 230, 240, 250 from the other snare loops along the longitudinal axis of the elongate shaft 210. In other embodiments the loops 230, 240, 250 may be positioned at angles other than perpendicular with respect to the longitudinal axis of the elongate shaft 210, including embodiments where the snare loops 230, 240, 250 are not positioned at the same relative angle. Further, in some embodiments the snare device may be configured with more than three total snare loops, including embodiments with four, five, and six snare loops. Each of these snare loops, including the third snare loop 250 may or may not be associated with an intermediate portion. Furthermore, each snare loop may be associated with a different elongate shaft in some embodiments. Additionally, in some embodiments, a snare device may comprise multiple shafts with one or more loops coupled to each shaft.

Figure 2B:
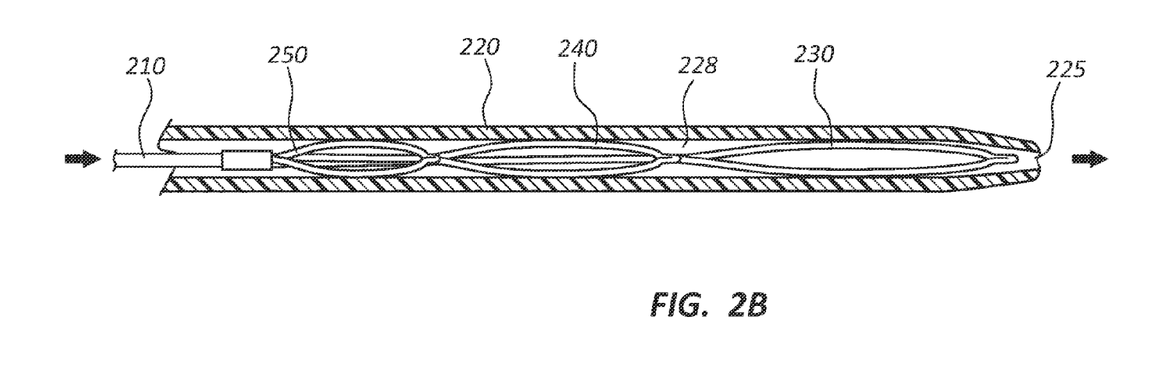
FIG. 2B is a cross-sectional view of the snare device of FIG. 2A in a fully retracted configuration.

FIG. 2B is a cross-sectional view of the snare device of FIG. 2A, disposed within an outer sheath 220, with the snare loops 230, 240, 250 in a fully retracted configuration. In the embodiment of FIG. 2B, each of the snare loops 230, 240, 250 is coupled, either directly or by an intermediate portion, to the elongate shaft 210. Thus, displacing the elongate shaft 210 with respect to the outer sheath 220 displaces all of the loops 230, 240, 250 within the sheath lumen 228.

Figure 2C:
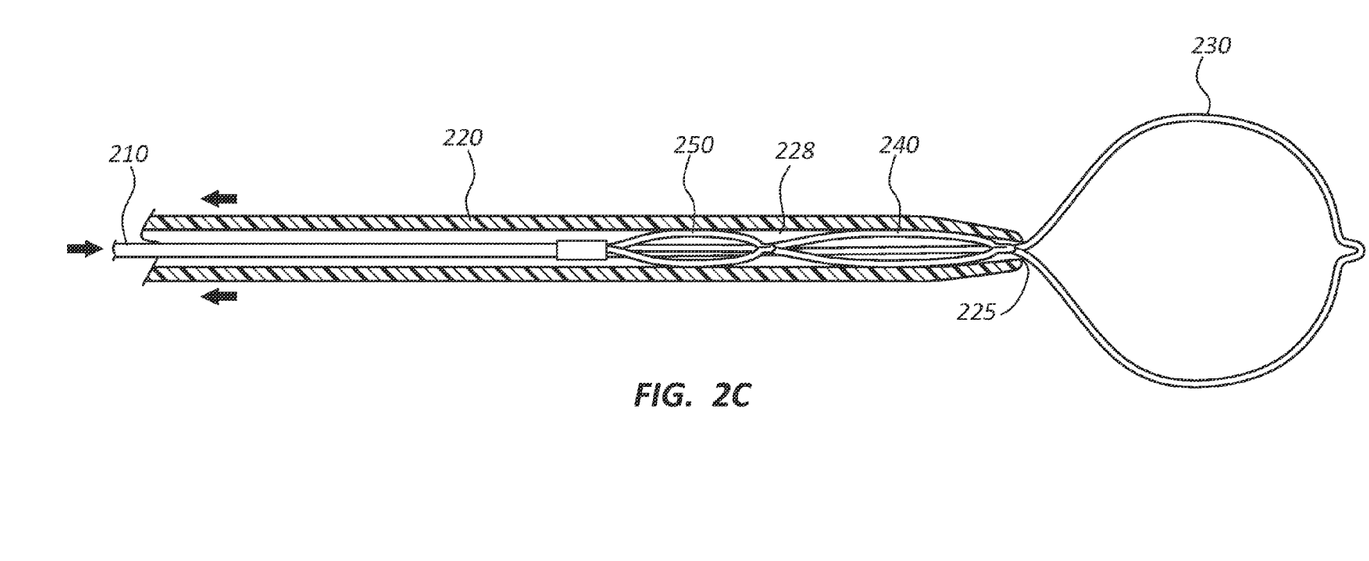
FIG. 2C is a cross-sectional view of the snare device of FIGS. 2A and 2B in a first partially deployed configuration.
Figure 2D:
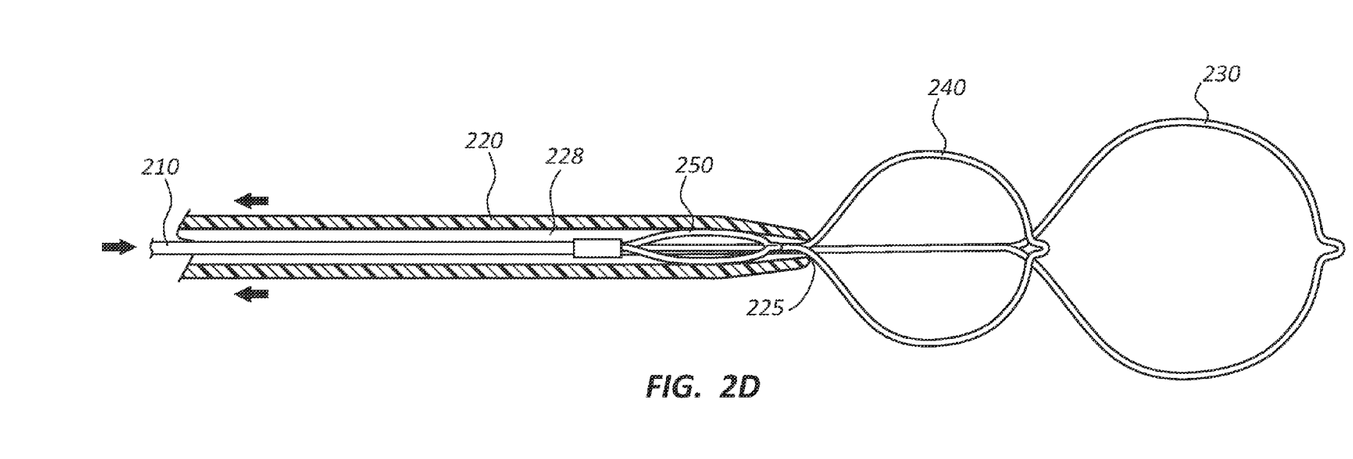
FIG. 2D is a cross-sectional view of the snare device of FIGS. 2A-2C in a second partially deployed configuration.
Figure 2E:
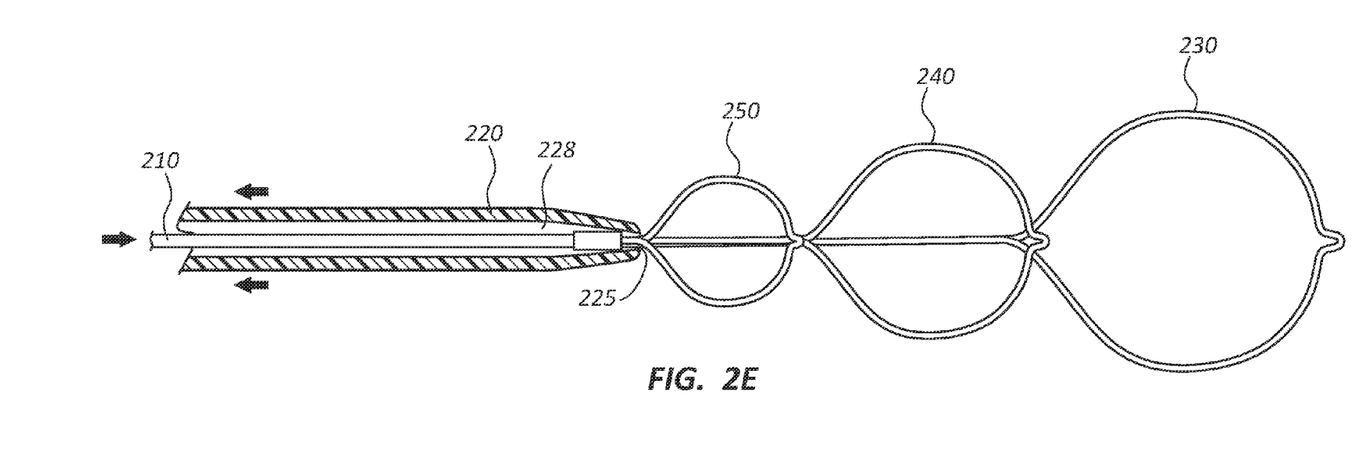
FIG. 2E is a cross-sectional view of the snare device of FIGS. 2A-2D in a third partially deployed configuration.

FIGS. 2B-2E are cross-sectional views of the snare device of FIGS. 2A and 2B in four configurations of relative deployment of the snare loops 230, 240, 250. As indicated by the arrows in each of the figures, displacing the elongate shaft 210 distally with respect to the outer sheath 220 also displaces the snare loops 230, 240, 250. FIG. 2C illustrates the first snare loop 230 deployed through the distal opening 225 in the elongate sheath, while FIGS. 2D and 2E illustrate the second 240 and third 250 loops, respectively, also deployed from the outer sheath 220.

In certain therapies a practitioner may therefore deploy multiple loops as necessary for the particular therapy. For example, a practitioner may deploy the first snare loop 230 by displacing the elongate shaft 210. Once deployed a practitioner may then determine whether the first snare loop 230 is appropriate for the particular therapy. In instances where, for example, a different snare loop may be better configured for the particular therapy, a practitioner could deploy the second 240 and/or third 250 snare loops as needed or desired. These snare loops may be configured with different sizes, shapes, orientations, and so forth.

Figure 3A:
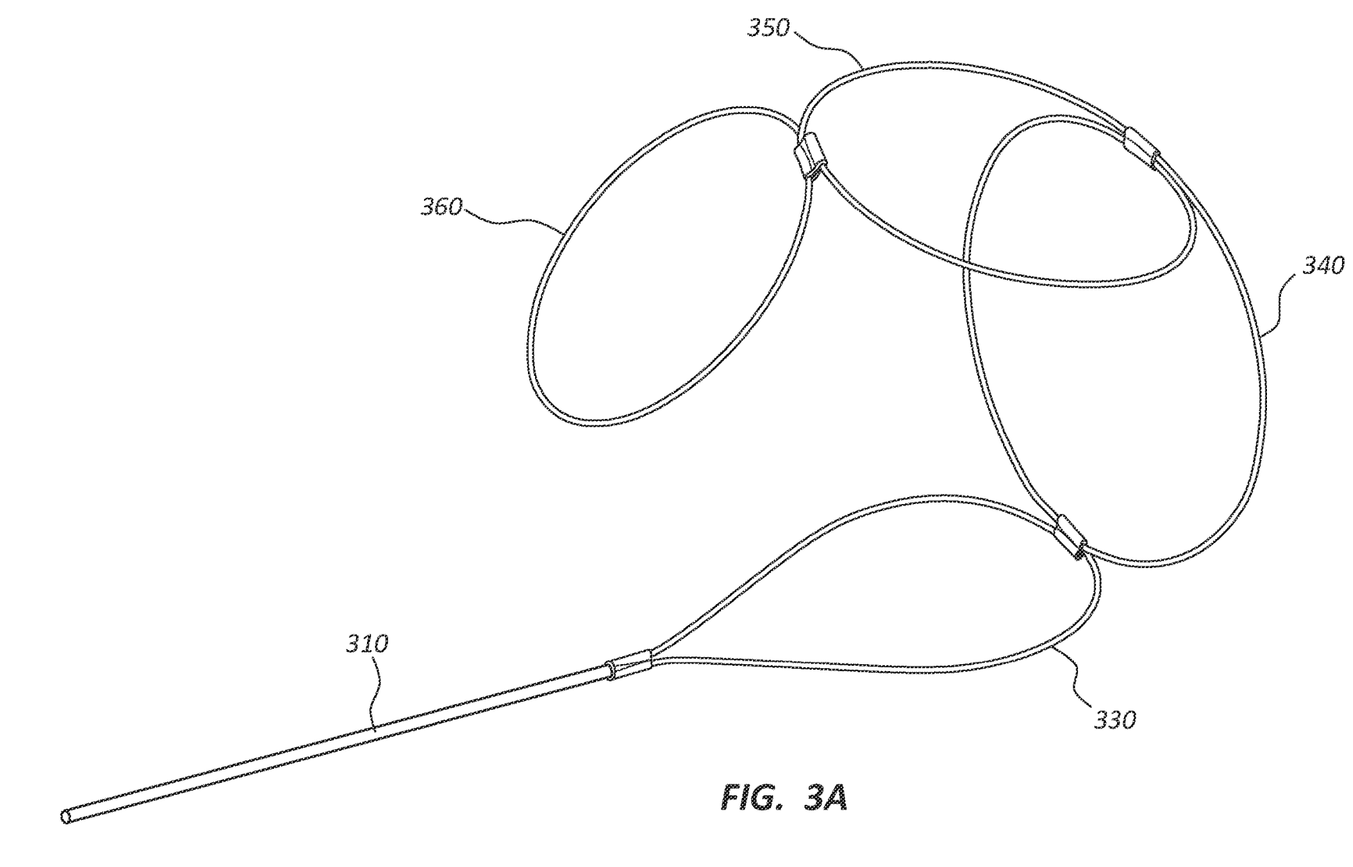
FIG. 3A is a perspective view of a snare device comprising four snare loops coupled to adjacent loops.

FIG. 3A is a perspective view of a snare device comprising four snare loops coupled to adjacent loops. In the embodiment of FIG. 3A, the first snare loop 330 is coupled directly to the elongate shaft 310, the second snare loop 340 is coupled to the first snare loop 330, the third snare loop 350 is coupled to the second snare loop 240, and the fourth snare loop 360 is coupled to the third snare loop 350. Further, each adjacent snare loop is disposed substantially perpendicular to the one or two loops coupled adjacent thereto. In alternate embodiments, the angle between adjacent loops may be larger or smaller, including embodiments where the angles between each adjacent loop are not the same for all loops of the device. Additionally, in some embodiments the snare loops may configured to be of different sizes, including embodiments where the snare loops are arranged by size and embodiments where they are not.

Figure 3B:
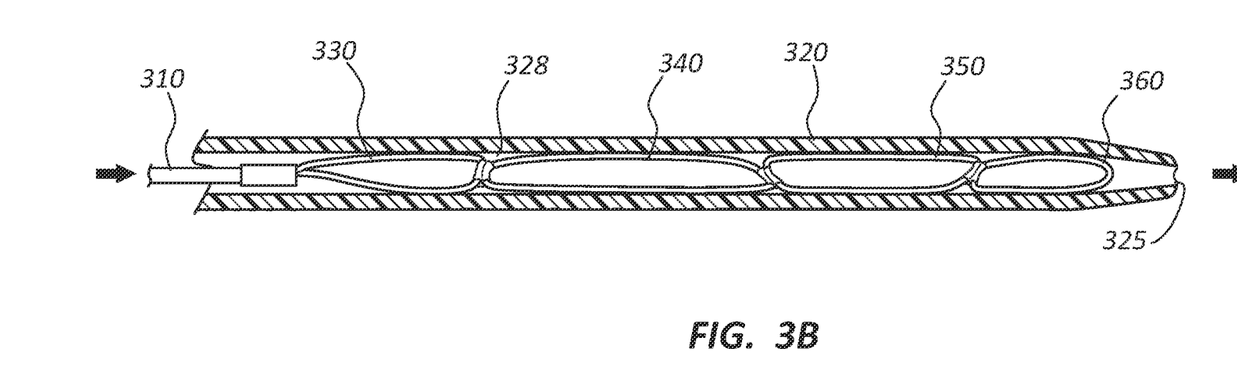
FIG. 3B is a cross-sectional view of the snare device of FIG. 3A in a fully retracted configuration.

FIG. 3B is a cross-sectional view of the snare device of FIG. 3A, disposed within an outer sheath 320, with the snare loops 330, 340, 350, 360 in a fully retracted configuration.

In the embodiment of FIG. 3B, each of the snare loops 330, 340, 350, 360 is coupled, either directly or by connection to another loop, to the elongate shaft 310. Thus, displacing the elongate shaft 310 with respect to the outer sheath 320 displaces all of the loops 330, 340, 350, 360 within the sheath lumen 328.

Figure 3C:
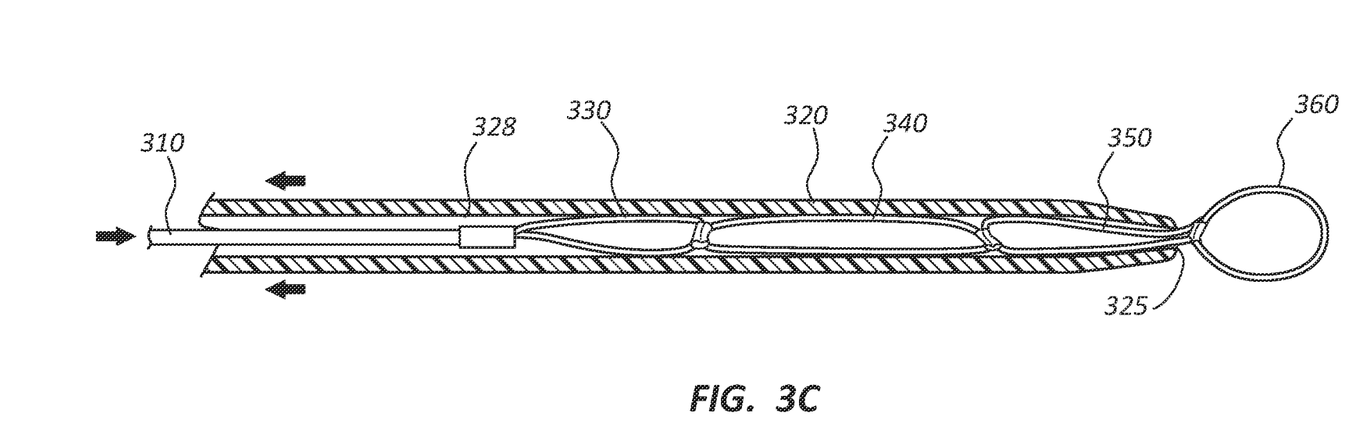
FIG. 3C is a cross-sectional view of the snare device of FIGS. 3A-3B in a first partially deployed configuration.
Figure 3D:
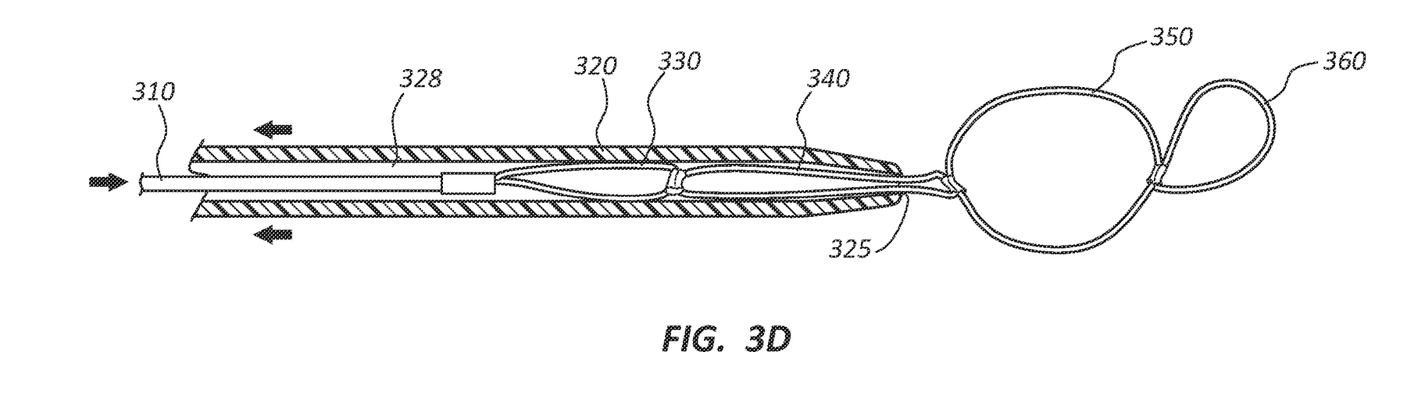
FIG. 3D is a cross-sectional view of the snare device of FIGS. 3A-3C in a second partially deployed configuration.
Figure 3E:
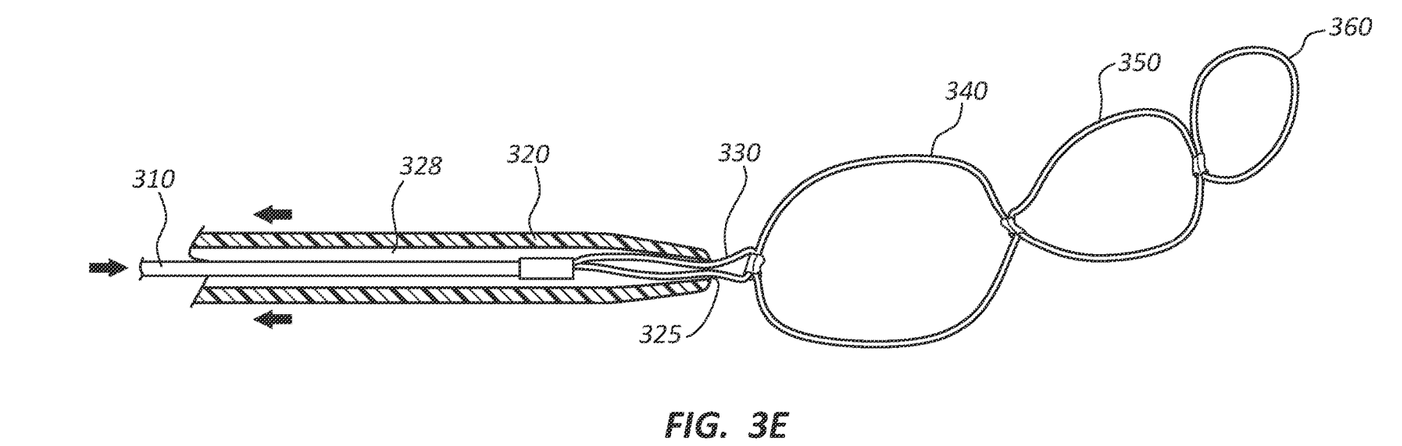
FIG. 3E is a cross-sectional view of the snare device of FIGS. 3A-3D in a third partially deployed configuration.

FIGS. 3B-3E are cross-sectional views of the snare device of FIGS. 3A and 3B in four configurations of relative deployment of the snare loops 330, 340, 350, 360. As indicated by the arrows in each of the figures, displacing the elongate shaft 310 distally with respect to the outer sheath 320 also displaces the snare loops 330, 340, 350, 360. FIG. 3C illustrates the fourth snare loop 360 deployed through the distal opening 325 in the elongate sheath, while FIGS. 3D and 3E illustrate the third 350 and second 340 loops, respectively, also deployed from the outer sheath 320.

As with the other embodiments discussed herein, a practitioner may select any of the loops as desired for the therapy to subsequently deploy some or all of the loops of the snare device. A practitioner may desire an alternate snare loop based on the size, shape, or orientation (for example) of the snare loops of the device. As with all embodiments discussed herein, each snare loop associated with a particular device may vary from other snare loops associated with the same device, by size, shape, orientation, material, and so forth.

Figure 4A:
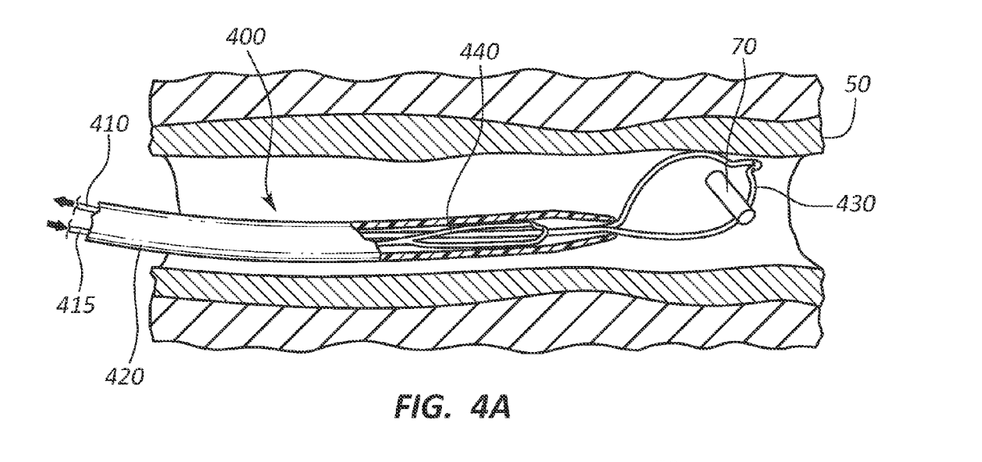
FIG. 4A is a side view of another embodiment of a snare device, in a first configuration, disposed within a cross-sectional view of a body lumen.
Figure 4B:
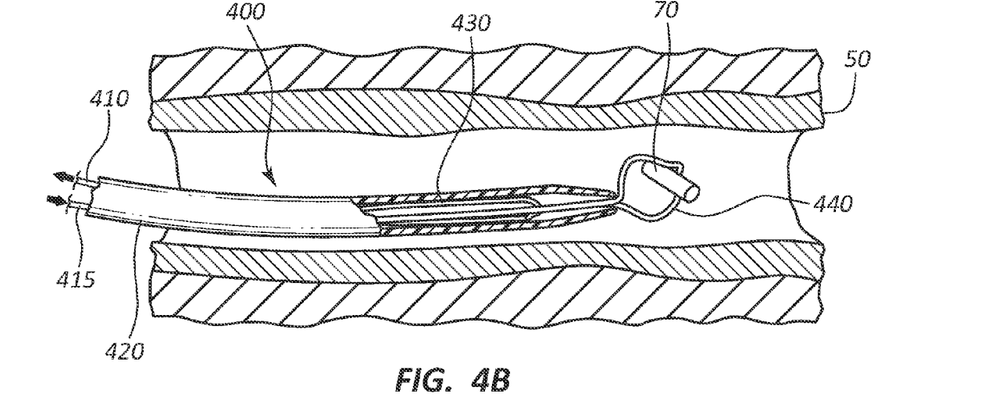
FIG. 4B is a side view of the snare device of FIG. 4A, in a second configuration, disposed within a cross-sectional view of the body lumen of FIG. 4A.
Figure 4C:
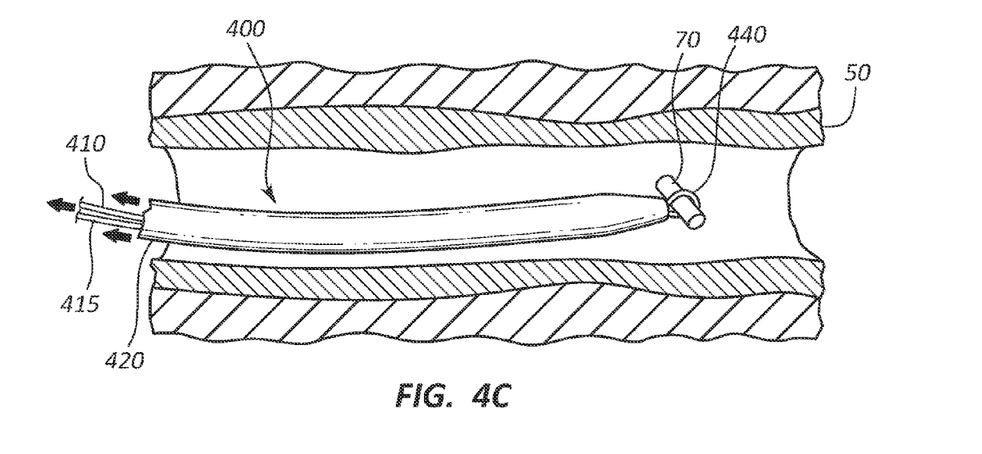
FIG. 4C is a side view of the snare device of FIGS. 4A and 4B, in a third configuration, disposed within a cross-sectional view of the body lumen of FIGS. 4A and 4B.

FIGS. 4A-4C are side views of another embodiment of a snare device 400 disposed within a cross-sectional view of a body lumen 50. These figures illustrate an exemplary procedure that may be performed utilizing a multiple loop snare device such as device 400. As with the snare device 100 of FIGS. 1A-1C, the snare device 400 shown in FIGS. 4A-4C comprises two elongate shafts 410, 415 and two snare loops 430, 440 disposed within an outer sheath 420. It will be appreciated by one of skill in the art having the benefit of this disclosure, that analogous procedures performed using analogous methods are also relevant to each embodiment disclosed herein.

FIG. 4A illustrates how a practitioner may initially deploy the first snare loop 430 as part of the procedure. In some instances a practitioner may directly use the first snare loop 430 to complete the procedure. In other instances, a practitioner may desire to use different snare loop (e.g. a smaller loop, a loop of a different shape, and so on) than the loop initially deployed. For example, in the process shown in FIGS. 4A and 4B a practitioner may determine that the first snare loop 430 is too large to properly perform the procedure. The practitioner may thus retract the first snare loop 430 and deploy the smaller second snare loop 440 as shown in FIG. 4B.

The exemplary procedure shown in FIGS. 4A-4C involves capturing a fragment 70 disposed within the body lumen 50. As illustrated in FIGS. 4B and 4C a practitioner may utilize a snare to capture a fragment 70 by surrounding the fragment 70 with a snare loop (such as the second snare loop 440) then partially retract that loop to capture the fragment 70. As indicated by the arrows in FIG. 4C the entire snare device 400 and the fragment 70 may then be withdrawn from the body lumen 50. Notwithstanding this specific example, snare devices as described herein may be used in any therapy which may utilize a snare loop, for example, cutting material (such as polyps), removing or repositioning stents or other implantable devices, capturing fragments, and so on.

The examples and embodiments disclosed herein are to be construed as merely illustrative and exemplary, and not a limitation of the scope of the present disclosure in any way.

It will be apparent to those having skill in the art, with the aid of the present disclosure, that changes may be made to the details of the above-described embodiments without departing from the underlying principles of the disclosure herein. It is intended that the scope of the invention be defined by the claims appended hereto and their equivalents.

The invention claimed is:

1. A snare device comprising:
an outer sheath comprising a lumen;
an elongate shaft at least partially disposed within the sheath lumen;
a first intermediate portion coupled to and extending distally from a distal end of the elongate shaft, the first intermediate portion including a first intermediate leg and a second intermediate leg, wherein the first intermediate leg is disposed substantially parallel with the second intermediate leg;
a first snare loop having a first end and a second end, wherein the first end of the first snare loop is coupled to a distal end of the first intermediate leg, and wherein the second end of the first snare loop is coupled to a distal end of the second intermediate leg;
a second snare loop having a first end and a second end, wherein the first end of the second snare loop and the second end of the second snare loop meet at and are coupled to the distal end of the elongate shaft at a position adjacent a proximal end of the first intermediate portion;
wherein the second snare loop is indirectly coupled to the first snare loop via the elongate shaft;
wherein the first intermediate portion is separate from the second snare loop; and
wherein the first snare loop and the second snare loop are configured to be disposed in a retracted configuration within the sheath lumen and a deployed configuration outside of the outer sheath.

2. The snare device of claim 1, wherein the first snare loop and the second snare loop comprise different sizes of loops.

3. The snare device of claim 1, further comprising a third snare loop coupled to the elongate shaft.

4. The snare device of claim 1, wherein the second snare loop is directly coupled to the elongate shaft.

5. The snare device of claim 1, further comprising a second intermediate portion extending distally from the distal end of the elongate shaft wherein the second intermediate portion is coupled to the elongate shaft and the second snare loop.

6. The snare device of claim 5, further comprising a third snare loop coupled to the elongate shaft.

7. The snare device of claim 6, wherein the first snare loop, the second snare loop, and the third snare loop are each disposed perpendicular to the axis of the elongate shaft when the snare device is in a fully deployed configuration.

8. The snare device of claim 6, wherein the first snare loop, the second snare loop, and the third snare loop are positioned proximally to distally according to size.

9. The snare device of claim 1, wherein the first snare loop and the second snare loop are configured to be simultaneously disposed within the sheath lumen.

10. The snare device of claim 1, wherein an entirety of the first snare loop is disposed distal of the second snare loop when the first snare loop and the second snare loop are both deployed.

11. A method of deploying a snare device, comprising:
obtaining the snare device of claim 1;
inserting the snare device into a body lumen of a patient; and
deploying at least one snare loop by displacing the elongate shaft relative to the outer sheath.

12. The method of claim 11, wherein deploying at least one snare loop comprises initially deploying the first snare loop.

13. The method of claim 12, further comprising determining whether the first snare loop is appropriate for a particular therapy.

14. The method of claim 11, wherein deploying at least one snare loop comprises serially deploying the first and second snare loops.

15. The method of claim 11, wherein the first snare loop and the second snare loop comprise different sizes of loops.

16. The method of claim 11, further comprising a third snare loop coupled to the elongate shaft.

17. The method of claim 11, wherein an entirety of the first snare loop is disposed distal of the second snare loop when the first snare loop and the second snare loop are both deployed.

* * * * *